(12) United States Patent  
Welch et al.

(10) Patent No.: US 9,937,321 B2  
(45) Date of Patent: Apr. 10, 2018

(54) INTRODUCER SHEATH FOR RADIAL ARTERY ACCESS

(71) Applicant: GMedix, Inc., Plymouth, MN (US)

(72) Inventors: Jeffrey M. Welch, Maple Grove, MN (US); Gregg Stuart Sutton, Plymouth, MN (US)

(73) Assignee: NorMedix, Inc., Plymouth, MN (US)

( * ) Notice: Subject to any disclaimer, the term of this patent is extended or adjusted under 35 U.S.C. 154(b) by 40 days.

(21) Appl. No.: 14/900,729

(22) PCT Filed: Jun. 27, 2014

(86) PCT No.: PCT/US2014/044519  
§ 371 (c)(1),  
(2) Date: Dec. 22, 2015

(87) PCT Pub. No.: WO2014/210427  
PCT Pub. Date: Dec. 31, 2014

(65) Prior Publication Data  
US 2016/0151605 A1  Jun. 2, 2016

Related U.S. Application Data

(60) Provisional application No. 61/840,764, filed on Jun. 28, 2013.

(51) Int. Cl.  
*A61M 25/00* (2006.01)  
*A61M 5/00* (2006.01)  
*A61M 25/01* (2006.01)  
*A61M 25/06* (2006.01)

(52) U.S. Cl.  
CPC ...... *A61M 25/0105* (2013.01); *A61M 25/005* (2013.01); *A61M 25/0045* (2013.01); *A61M 25/0662* (2013.01); *A61M 25/0041* (2013.01)

(58) Field of Classification Search  
CPC .......... A61M 25/0045; A61M 25/0041; A61M 25/005; A61M 25/0105; A61M 25/0662  
USPC ......................................... 604/526  
See application file for complete search history.

(56) References Cited

U.S. PATENT DOCUMENTS

| | | | |
|---|---|---|---|
| 5,938,587 A | 8/1999 | Taylor et al. | |
| 6,197,014 B1 * | 3/2001 | Samson | A61M 25/005 604/524 |
| 6,689,120 B1 * | 2/2004 | Gerdts | A61M 25/005 604/526 |

(Continued)

FOREIGN PATENT DOCUMENTS

| | | |
|---|---|---|
| CN | 105579091 A | 5/2016 |
| EP | 1068876 A2 | 1/2001 |

(Continued)

OTHER PUBLICATIONS

"European Application Serial No. 14818501.0, Extended European Search Report dated Feb. 2, 2017", 11 pgs.

(Continued)

*Primary Examiner* — Jason Flick  
(74) *Attorney, Agent, or Firm* — Schwegman Lundberg & Woessner, P.A.

(57) ABSTRACT

Embodiments of the invention include an introducer for introducing interventional catheters into the vasculature comprising a distal tip, a proximal end, a structural layer, an inner layer, and an outer layer. Other embodiments are also included herein.

28 Claims, 7 Drawing Sheets

(56) References Cited

U.S. PATENT DOCUMENTS

2010/0331936 A1* 12/2010 Perrey .................... A61N 1/056
                                                    607/116
2013/0172851 A1*  7/2013 Shimada ........... A61M 25/0053
                                                    604/508
2017/0252535 A1   9/2017 Ganske et al.

FOREIGN PATENT DOCUMENTS

WO    WO-2005072806 A2    8/2005
WO    WO-2013003835 A1    1/2013
WO    WO-2014210427      12/2014

OTHER PUBLICATIONS

"European Application Serial No. 14818501.0, Response filed Aug. 11, 2016 to Communication pursuant to Rules 161(1) and 162 EPC dated Feb. 12, 2016", 7 pgs.
"European Application Serial No. 14818501.0, Response filed Sep. 4, 2017 to Extended European Search Report dated Feb. 2, 2017", 7 pgs.
"International Application Serial No. PCT/US2014/044519, International Preliminary Report on Patentability dated Jan. 7, 2016", 13 pgs.
"International Application Serial No. PCT/US2014/044519, International Search Report dated Oct. 21, 2014", 4 pgs.
"International Application Serial No. PCT/US2014/044519, Written Opinion dated Oct. 21, 2014", 11 pgs.

* cited by examiner

INTRODUCER SHEATH FOR RADIAL ARTERY ACCESS

CLAIM OF PRIORITY

This application claims the benefit of U.S. Provisional Application No. 61/840,764, filed Jun. 28, 2013, the content of which is herein incorporated by reference in its entirety.

FIELD OF THE INVENTION

The present invention relates to an arterial sheath introducer. More specifically, the present invention relates to an arterial sheath introducer intended to facilitate introduction of interventional catheter devices through the skin and into the arterial system.

BACKGROUND OF THE INVENTION

Currently, vascular introducer sheaths used to access radial or femoral arteries suffer from various limitations. These include buckling or "roll-back" of the very distal tip upon entry into the skin. This is caused by a poor or abrupt transition or step between the introducer tip and the dilator that is inside the introducer to provide a transition from the guidewire to the sheath. Roll-back can also be caused by inadequate mechanical structure of the sheath tip.

Another limitation of current vascular introducer sheaths is the overall diameter of the introducer can be too large, such that excessive bleeding upon removal and/or arterial spasm during use can be caused. This limitation can be due to excessive wall thickness of the introducer related to current introducer construction methods.

A further limitation of current introducer is kinking or buckling during manipulation, insertion, or withdrawal of the catheter through the sheath or due to excessive cutaneous tissue thickness. The kinking and buckling of the introducer can be inherent in the construction and design of currently available introducer.

SUMMARY OF THE INVENTION

Embodiments of the invention include a radial artery catheter introducer sheath for introducing interventional catheters into the vasculature comprising: a main tubular shaft comprising a distal tip, a proximal end, an inner layer, a main structural layer and an outer layer; wherein the inner layer comprises one or more layers of polymer with a thickness of 0.001-0.005 inches, the main structural layer comprises one or more metallic helically wound multi-filar wires with a wall thickness of 0.0015 inches to 0.010 inches; wherein the outer layer comprises an outer polymer jacket that at least partially covers the inner layer at the distal tip, and the outer polymer jacket is coupled to the main structural layer; wherein the outer polymer jacket has a thickness of 0.001 inches to 0.010 inches; wherein the distal tip comprises 2 or more layers, these layers formed of the outer polymer and inner polymer, and the distal tip has a length of 0.05 inches and 0.30 inches.

In an embodiment, the main tubular shaft can have an outer diameter of 0.060 inches to 0.160 inches. The main tubular shaft can comprise an inner polymer layer, a main structural layer comprised of multi-filar wires that have been swaged into a rectangular cross-section and covered with a metallic wire braid and an outer polymer jacket. The distal tip can also comprise two or more layers, such as a layer of PTFE and a layer of Pebax.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

BRIEF DESCRIPTION OF THE FIGURES

The invention may be more completely understood in connection with the following drawings, in which.

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION OF THE INVENTION

The embodiments of the present invention described herein are not intended to be exhaustive or to limit the invention to the precise forms disclosed in the following detailed description. Rather, the embodiments are chosen and described so that others skilled in the art can appreciate and understand the principles and practices of the present invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

The device of this invention solves the problems associated with current vascular introducer sheaths by providing novel improved design, construction and materials.

Figure 1:
FIG. 1 is a view of an introducer, according to an embodiment.
Figure 2:
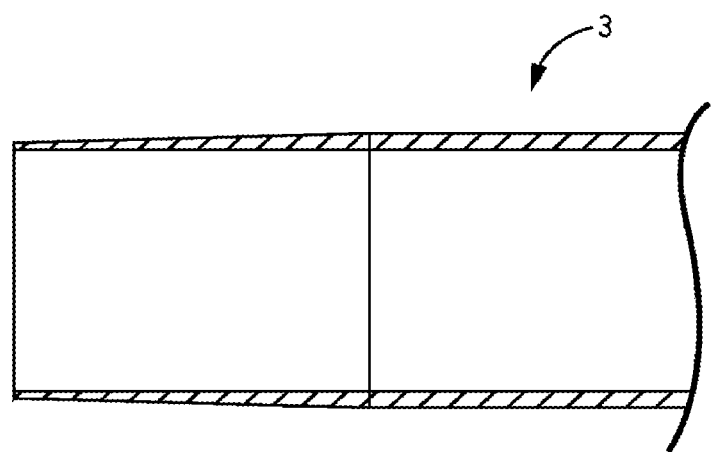
FIG. 2 is a cross-section view of a portion of an introducer, according to an embodiment.

FIG. 1 shows an introducer 100. The introducer 100 can comprise a composite built main tubular shaft. The main tubular shaft can be configured to be slideable, such that an inner dilator can slide through the main tubular shaft. The main tubular shaft can be configured to closely fit an inner dilator for delivery through the skin and into an artery. An inner dilator can be mounted inside the introducer 100, such as during insertion, such as to allow a smooth transition from a guidewire to the introducer 100. In an embodiment, the main tubular shaft can have an outer diameter of 0.060 inches or more. In an embodiment, the main tubular shaft can have an outer diameter of 0.160 inches or less. In an embodiment, the main tubular shaft can have a length of 15 cm or more. In an embodiment, the main tubular shaft can have a length of 205 cm or less. The main tubular shaft can comprise a wound metal structural layer 1. The structural layer 1 can be jacked with a thin wall polymer. The structural layer 1 can comprise a multi-filar metallic helical wound structure. The multi-filar structure can comprise stainless steel.

In an embodiment, the structural layer 1 can comprise 12 or more filars. In an embodiment, the structural layer 1 can comprise 18 or fewer filars. In an embodiment, the multi-filar structure can be swaged such that each wire has a rectangular cross-section, such that it can result in a very close fitting wire matrix between adjacent wires. The multi-filar structure can comprise non-swaged wires. The multi-filar structure can comprise a wire with a round (such as circular, oval, or elliptical) cross-section. The multi-filar structure can comprise a wire with a square or rectangular cross-section. The multi-filar structure can comprise welded ends. The multi-filar structure can comprise a PTFE coating. In an embodiment, the multi-filar wires can comprise a PTFE coating prior to forming the multi-filar structure.

In an embodiment, the structural layer 1 can define a center lumen, such as to allow an inner dilator to pass through the introducer 100. The structural layer 1 can have a thickness of 0.0015 inches or more. The structural layer 1 can have a thickness of 0.003 inches or less. In an embodiment, the structural layer 1 can have a thickness of 0.010 inches or less. The structural layer 1 can provide a significant improvement in mechanical integrity of the sheath compared to existing introducer sheaths with respect to kinking, buckling, flexibility, radial strength and maintaining cross-sectional circularity of the sheath.

The introducer 100 can include a distal end and a proximal end 6. In an embodiment, the distal end of the introducer 100 can be curved, such as to conform to a portion of a patient's anatomy. In an embodiment, the structural layer can be curved to the desired shape and heat processed such that the structural layer holds the desired curve shape.

Figure 8:
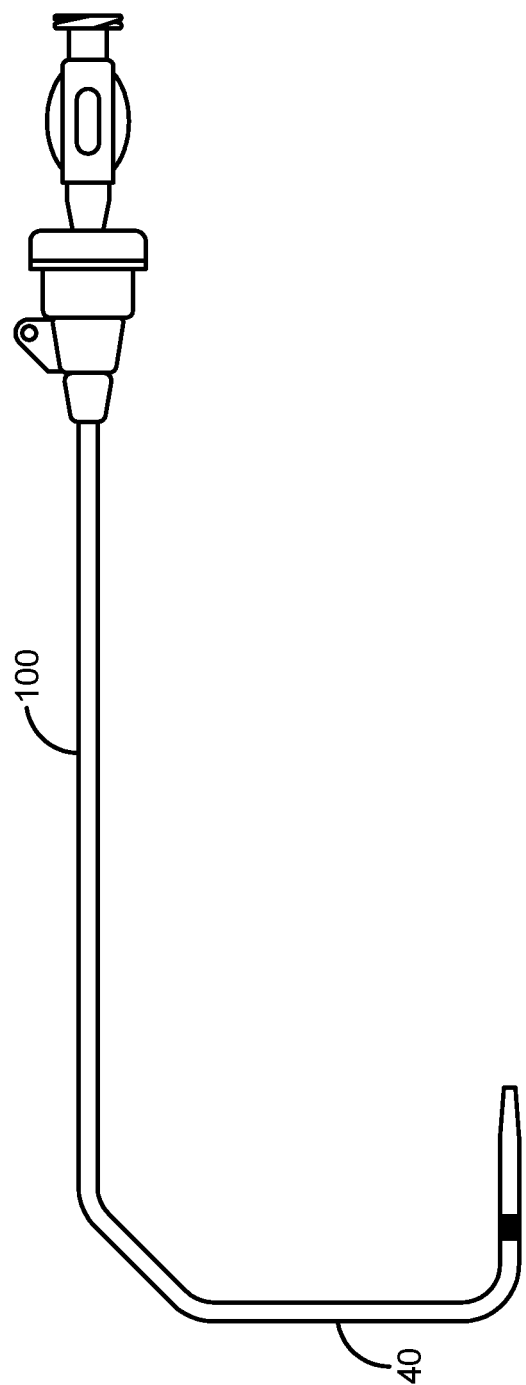
FIG. 8 is a view of an introducer with a curved distal end, according to an embodiment.

One example of the introducer 100 including a curved distal end 40 is shown in FIG. 8. As shown, the curved distal end 40 is provided with a curved profile, for instance, curved to conform to the anatomy of a patient. The curved profile is, in an example, formed in the distal end through shaping and heat processing.

The introducer 100 can further comprise an outer layer 2. The outer layer can comprise an outer polymer jacket. The outer polymer jacket can substantially cover the outside surface of the structural layer 1. The outer polymer jacket can comprise one or more of the following: PTFE, Pebax, nylon and Polyurethane. In an embodiment, the outer polymer jacket 2 comprises one or more layers or segments of different polymers. In an embodiment, the outer polymer jacket comprises two or more layers of Pebax. The outer polymer jacket can comprise or be coated with a hydrophilic polymer. The outer polymer jacket can be coupled to the structural layer 1, such as by thermal polymer heat-shrinking or reflow. Heat shrinking the outer polymer jacket can allow the outer polymer jacket 2 to be formed tightly onto the structural layer 1. In an embodiment, the outer polymer jacket can have a thickness of 0.001 inches or more. In an embodiment, the outer polymer jacket can have a thickness of 0.003 inches or less. In an embodiment, the outer polymer jacket can have a thickness of 0.010 inches or less.

The introducer 100 can further comprise an inner layer 7. The inner layer 7 can comprise an inner polymer jacket. The inner polymer jacket can substantially cover a surface of the structural layer 1, such as the inner surface. The inner polymer jacket can comprise one or more of the following: PTFE, Pebax, nylon and Polyurethane. In an embodiment, the inner polymer jacket comprises one or more layers or segments of different polymers. In an embodiment, the inner polymer jacket comprises two or more layers of Pebax. The inner polymer jacket can comprise or be coated with a hydrophilic polymer. The inner polymer jacket can be coupled to the structural layer 1, such as by thermal polymer reflow. In an embodiment, the inner polymer jacket can have a thickness of 0.001 inches or more. In an embodiment, the inner polymer jacket can have a thickness of 0.005 inches or less. In an embodiment, the inner polymer jacket can have a thickness of 0.010 inches or less.

In an embodiment, the lamination of the structural layer 1, the outer layer 2, and the inner layer 7 does not include fusion of the outer layer 2 and the inner layer 7. In an embodiment, the inner layer 7 and the outer layer 2 can be fused between and through the structural layer 1. In other implementations the outer layer and the inner layer are not fused together.

In some implementations the material forming the introducer, taken along a cross section of the introducer perpendicular to the central axis of the introducer, is from 40 to 60 percent metal. In other implementations the material forming the introducer, taken along a cross section of the introducer perpendicular to the central axis of the introducer, is from 20 to 60 percent metal. Alternatively the material forming the introducer, taken along a cross section of the introducer perpendicular to the central axis of the introducer, is greater than 20 percent metal.

The introducer 100 can further comprise a distal tip 3. The distal tip 3 can be tapered, such that the portion of the distal tip 3 closer to the proximal end 6 of the introducer 100 has a larger outer diameter than the distal end of the distal tip 3. The outer diameter of the distal end of the distal tip 3 can be configured to closely hug the outer diameter of an inner dilator.

The length of the distal tip 3 can be at least 0.05 inches. In an embodiment, the length of the distal tip 3 is 0.30 inches or less.

The distal tip 3 can comprise an inner tip layer and an outer tip layer. The inner tip layer can comprise PTFE and the outer tip layer can comprises Pebax. The distal tip 3 can comprise a gold coating. In an embodiment, the thickness of the gold coating is 0.5 mm or more. In an embodiment, the thickness of the gold coating is 2 mm or less. The distal tip 3 can comprise a composite of a thin sheath jacket layer on the inside of the tip and a reflowed polymer on the outside. A distal tip 3 comprising such a composite can results in a very close fitting (non-abrupt) transition from the inner dilator to the introducer 100, thus reducing potential introducer tip damage such as "roll-back" or buckling. The main tubular shaft can be coupled to the hemostatis valve 4.

Figure 3:
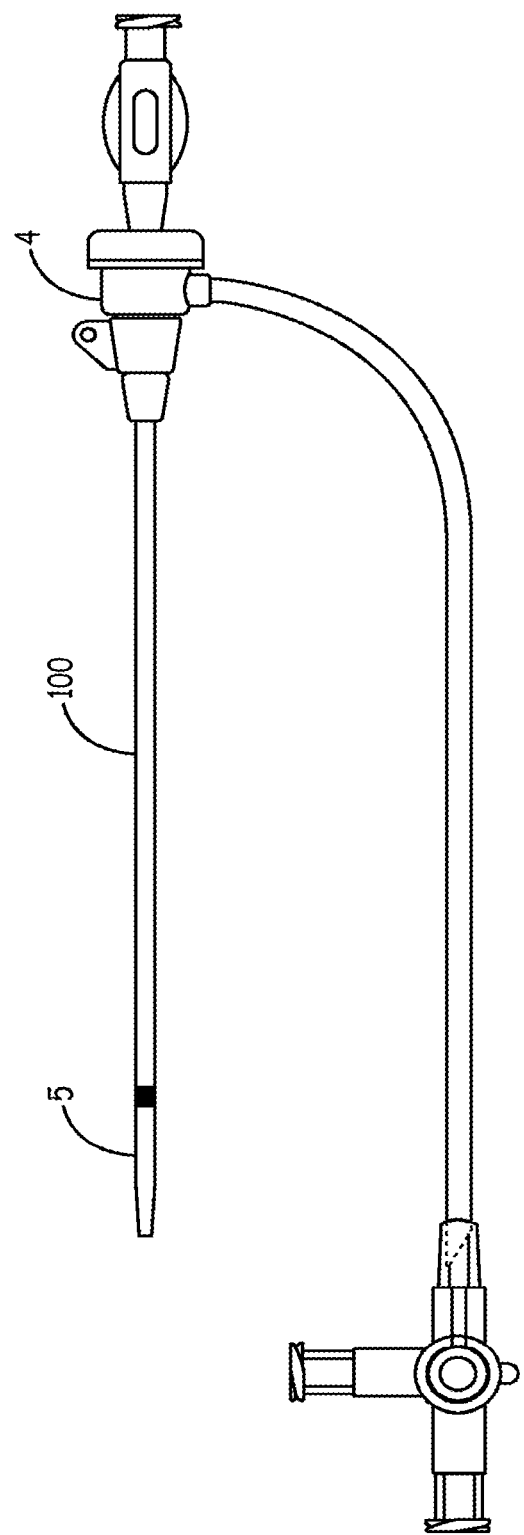
FIG. 3 is a view of an introducer along with other components it can be used with, according to an embodiment.

As shown in FIG. 3, the introducer 100 can also be configured to be used with standard components and elements familiar with those skilled in the art such as a hemostatis valve 4, an inner dilator 5, proximal hemostasis adaptor, side-port luer extension for flushing and a skin attachment means at the proximal adaptor. In an embodiment, an infusion port can be attached to the hemostatis valve 4, such as to allow infusion of media through the introducer 100.

Figure 4:
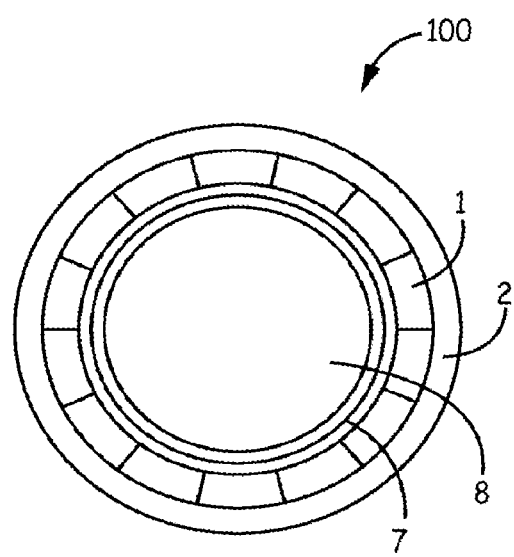
FIG. 4 is a view of a cross section of an introducer, according to an embodiment.
Figure 5:
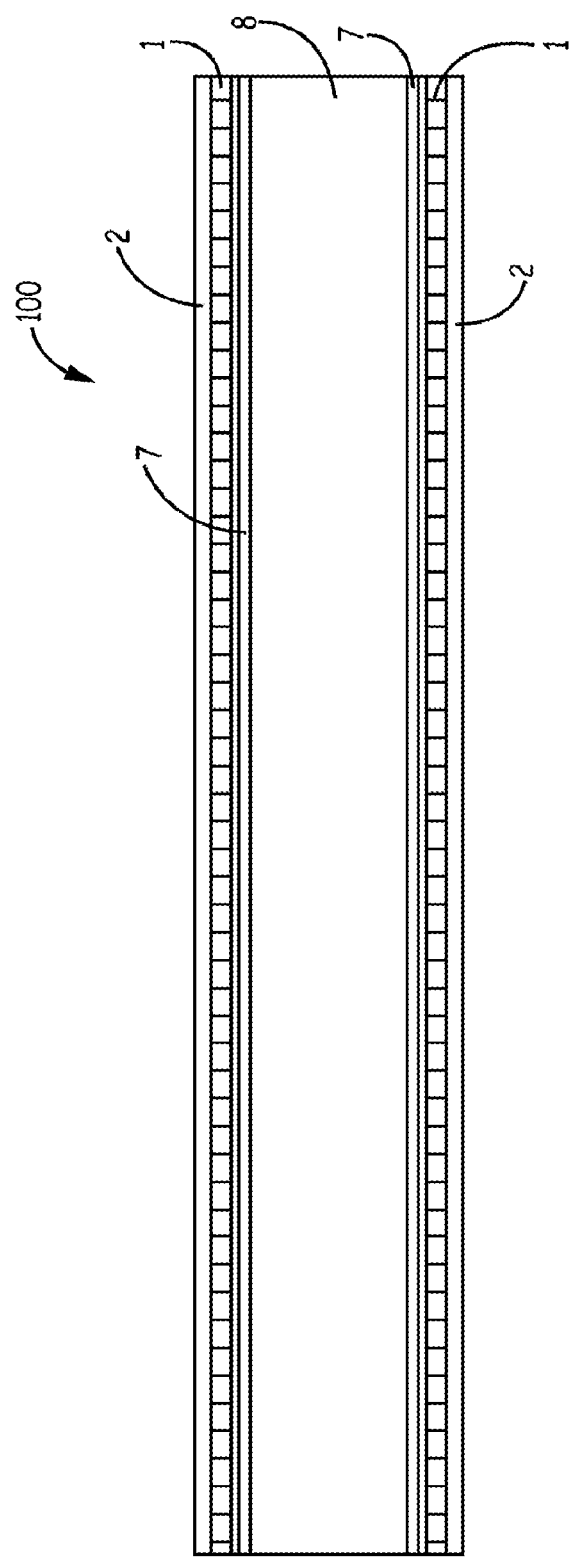
FIG. 5 is a view of a cross section of an introducer, according to an embodiment.

FIG. 4 shows a cross section of an introducer 100, according to an embodiment. FIG. 5 shows a cross section of a similar introducer 100. The introducer 100 can define a central lumen 8, such as to accommodate the passage of an object, such as a dilator. The introducer 100 can include a structural layer 1, an outer layer 2, and an inner layer 7. In an embodiment, the outer layer 2 can include two or more layers. In an embodiment, the inner layer 7 can include two or more layers.

Figure 6:
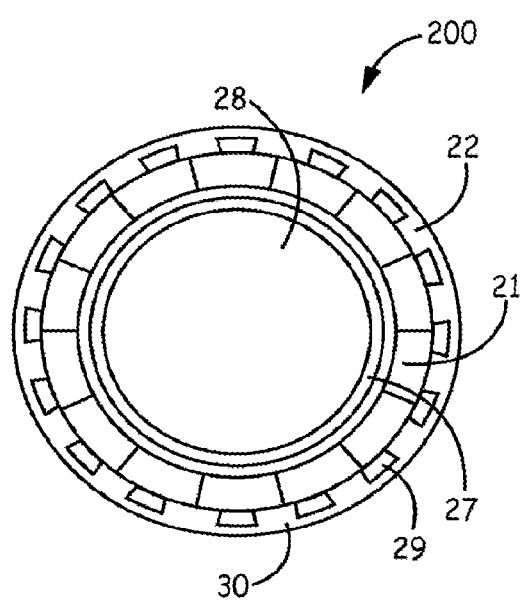
FIG. 6 is a view of a cross section of an introducer, according to an embodiment.
Figure 7:
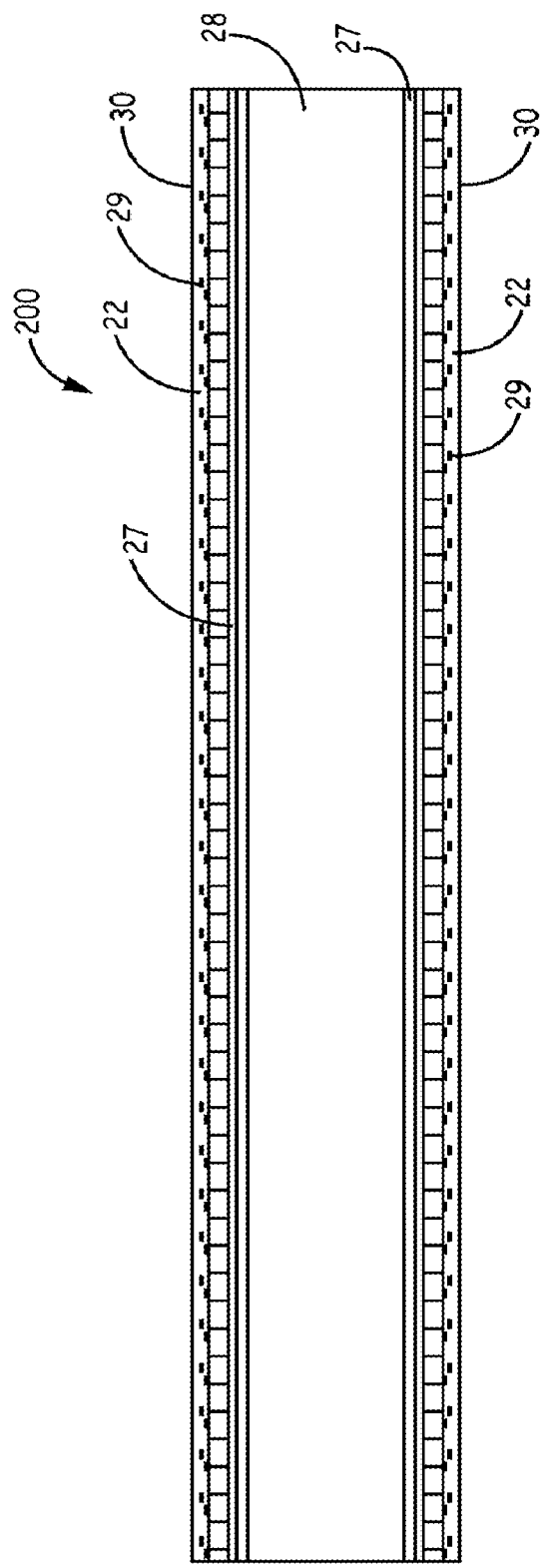
FIG. 7 is a view of a cross section of an introducer, according to an embodiment.

FIG. 6 shows a cross section of an introducer 200, according to an embodiment. FIG. 7 shows a cross section of a similar introducer 200. The introducer 200 can define a central lumen 28, such as to accommodate the passage of an object, such as a dilator. The introducer 200 can include a structural layer 21, an outer layer 22, and an inner layer 27. In an embodiment, the outer layer 22 can include two or more layers, such as braid 29 and a polymer layer 30. The braid 29 can be positioned between the polymer layer 30 and the structural layer 21. In an embodiment, the braid 29 can include metal. In an embodiment, the polymer layer 30 can fuse together with the braid 29, such that portions of the polymer layer 30 are disposed between or around portions of the braid 29.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

The invention claimed is:

1. A radial artery catheter introducer sheath for introducing interventional catheters into the vasculature comprising:
a main tubular shaft comprising a distal tip, a proximal end, a structural layer, an inner layer, and an outer layer;
wherein the structural layer comprises one or more metallic helically wound multi-filar wires with a wall thickness of 0.0015 inches to 0.010 inches, and each helically wound multi-filar wire includes a proximal edge and a distal edge, and each of the proximal and distal edges is coupled along a respective distal or proximal edge of proximate helically wound multi-filar wires, and the structural layer is heat processed to retain a curved distal end;
wherein the outer layer comprises an outer polymer jacket that at least partially covers the structural layer and the outer polymer jacket is coupled to the structural layer the outer polymer jacket having a thickness of 0.001 inches to 0.010 inches;
wherein the inner layer comprises an inner polymer jacket that at least partially covers the structural layer and the inner polymer jacket is coupled to the structural layer;
wherein the inner polymer jacket has a thickness of 0.001 inches to 0.010 inches; and
wherein the distal tip comprises an outer polymer and the distal tip has a length of 0.05 inches and 0.30 inches.

2. The introducer of claim 1, wherein the metal helically wound multi-filar layer comprises stainless steel.

3. The introducer of claim 1, wherein the multi-filar structure comprises 12 to 18 filars.

4. The introducer of claim 1, wherein the multi-filar structure wire is swaged so as to impart a rectangular cross-section and intimate fitting contact between adjacent wires.

5. The introducer of claim 1, wherein the main tubular shaft has an outer diameter of 0.060 inches to 0.115 inches.

6. The introducer of claim 1, wherein the outer polymer jacket comprises PTFE.

7. The introducer of claim 1, wherein the outer polymer jacket comprises nylon.

8. The introducer of claim 1, wherein the outer polymer jacket is coated with a hydrophilic polymer.

9. The introducer of claim 1, wherein the distal tip comprises an inner tip layer and an outer tip layer, wherein the inner tip layer comprises PTFE and the outer tip layer comprises a thermoplastic elastomer.

10. The introducer of claim 1, wherein the helically wound multi-filar wires comprise welded terminations.

11. The introducer of claim 1, wherein the distal tip comprises a gold coating, wherein the gold coating is between 0.5 mm to 2 mm.

12. The introducer of claim 1, wherein the outer polymer jacket comprises a thermoplastic elastomer.

13. The introducer of claim 1, wherein the outer polymer jacket comprises two layers of a thermoplastic elastomer.

14. The introducer of claim 1, wherein the outer jacket layer is heat shrinkable and configured to be formed tightly onto the helically wound multi-filar structure.

15. The introducer of claim 1, wherein the helically wound multi-filar structure wire has a rectangular cross-section.

16. The introducer of claim 1, wherein the helically wound multi-filar structure wire has a circular cross-section.

17. The introducer of claim 1, wherein the helically wound multi-filar structure wire has an oval or elliptical cross-section.

18. The introducer of claim 1, wherein the proximal end of the main tubular shaft is coupled to a hemostasis valve.

19. The introducer of claim 1, wherein the main tubular shaft is configured to be slideable and closely fit to an inner dilator for delivery through the skin and into the artery.

20. The introducer of claim 1, wherein the helically wound multi-filar structure wires comprise a PTFE coating prior to forming into a multi-filar configuration.

21. The introducer of claim 1, wherein the main tubular shaft has a length of 15 cm to 205 cm.

22. The introducer of claim 15, wherein the multi-filar structure has an intimate fitting contact between adjacent wires.

23. The introducer of claim 1, wherein the outer polymer jacket substantially covers the structural layer.

24. The introducer of claim 1, wherein the outer layer and the inner layer are isolated from each other.

25. The introducer of claim 1, wherein the material forming the introducer, taken along a cross section of the introducer perpendicular to the central axis of the introducer, is from 40 to 60 percent metal.

26. The introducer of claim 1, wherein the material forming the introducer, taken along a cross section of the introducer perpendicular to the central axis of the introducer, is from 20 to 60 percent metal.

27. The introducer of claim 1, wherein the material forming the introducer, taken along a cross section of the introducer perpendicular to the central axis of the introducer, is greater than 20 percent metal.

28. The introducer of claim 1, wherein the distal tip comprises 2 or more layers of outer polymer.

* * * * *

UNITED STATES PATENT AND TRADEMARK OFFICE
CERTIFICATE OF CORRECTION

| | | |
|---|---|---|
| PATENT NO. | : 9,937,321 B2 | Page 1 of 1 |
| APPLICATION NO. | : 14/900729 | |
| DATED | : April 10, 2018 | |
| INVENTOR(S) | : Welch et al. | |

It is certified that error appears in the above-identified patent and that said Letters Patent is hereby corrected as shown below:

On the Title Page

In item (71), in "Applicant", in Column 1, Line 1, delete "GMedix, Inc.," and insert --NorMedix, Inc.,-- therefor Signed and Sealed this
First Day of February, 2022

Drew Hirshfeld
*Performing the Functions and Duties of the*
*Under Secretary of Commerce for Intellectual Property and*
*Director of the United States Patent and Trademark Office*